United States Patent [19]
Bodenschatz et al.

[11] Patent Number: 6,120,470
[45] Date of Patent: Sep. 19, 2000

[54] SELF-ADHESIVE READY-TO-USE BANDAGE FOR ELBOWS

[75] Inventors: Stefan Bodenschatz; Peter Himmelsbach, both of Buxtehude, Germany

[73] Assignee: Beiersdorf AG, Hamburg, Germany

[21] Appl. No.: 08/964,926

[22] Filed: Nov. 5, 1997

[30] Foreign Application Priority Data

Nov. 13, 1996 [DE] Germany ............... 196 46 741

[51] Int. Cl.$^7$ ........................................ A61F 5/00
[52] U.S. Cl. ................. 602/20; 602/21; 602/52; 602/54; 602/57
[58] Field of Search ................. 602/20, 21, 52, 602/54, 57, 60–62, 64–66, 41, 58, 59, 79

[56] References Cited

U.S. PATENT DOCUMENTS 2,253,108  8/1941  Casey, Jr. .................... 602/59

*Primary Examiner*—Kim M. Lee
*Attorney, Agent, or Firm*—Norris, McLaughlin & Marcus, P.A.

[57] ABSTRACT

Ready-to-use bandage self-adhesively coated on one side for relieving and functionally restricting the elbow joint, having a substantially rectangular central part A which is at least partially inelastic in the transverse direction of the bandage and on which there are respectively arranged, directed upwards and downwards seen in the longitudinal direction, two elongate strips B, C, D and E.

3 Claims, 2 Drawing Sheets

SELF-ADHESIVE READY-TO-USE BANDAGE FOR ELBOWS

BACKGROUND OF THE INVENTION

The invention relates to a ready-to-use bandage which has a self-adhesive coating on one side and which is used for supporting and functionally restricting the elbow joint. The relief of the joint brought about as a result is used in particular for the treatment of extension trauma, irritations, for example of the capsular ligament apparatus, complaints concerning overstraining of the M. biceps brachii, M. brachialis, M. brachioradialis or Epicondylitis radialis.

The functional bandaging technique, so-called taping, is a common treatment method for the prevention and therapy of injuries, disorders and changes of the locomotor system. The aim of taping is to simulate specifically the individual soft parts and capsular ligament structures and selectively support their functions.

The tape bandage is applied in the form of several bands, so-called straps, in strip formation, using preferably inelastic material, sometimes combined with elastic material, and then performs the functions of supporting and relieving.

However, bandages of this type require specialist ability and a great deal of experience and therefore cannot generally be applied by someone inexperienced in taping.

DE-C 195 12 013 discloses a self-adhesive ready-to-use bandage which makes application easier and is intended for supporting and partially fixing the elbow joint, comprising an elongate strip which has an incision on one side in the longitudinal direction approximately up to the centre of the strip. Such a bandage is not suitable, however, for all indications encountered in medicine, in particular it is not designed for restricting the extension of the joint.

SUMMARY OF THE INVENTION

The object of the invention was therefore to develop a ready-to-use bandage which, by virtue of its configuration, supports and relieves the elbow joint and makes it possible to restrict the extension of the joint.

This object is achieved by a bandage which is coated on one side with a self-adhesive and has contiguous elongate strips, which are elastic in the longitudinal direction, for relieving and functionally restricting the elbow joint, comprising a substantially rectangular central part A having two opposite transverse sides and two opposite longitudinal sides; said elongate strips being arranged on each of said transverse sides.

DETAILED DESCRIPTION

Figure 1:
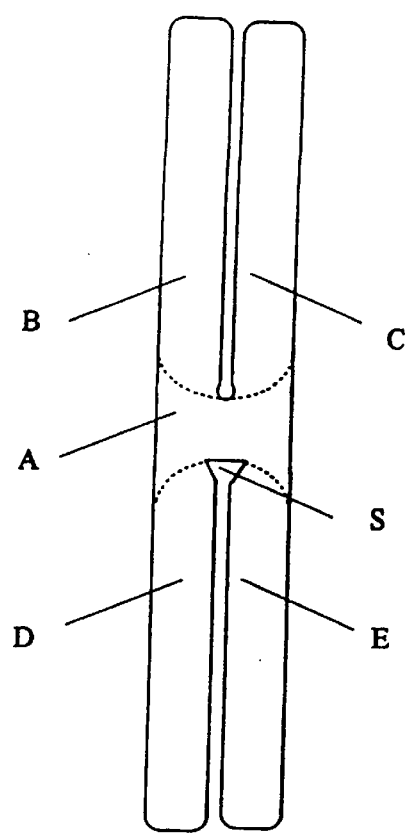

The central part A is preferably of an inelastic design, seen in the transverse direction of the bandage, but may also be only partially inelastic, for example in such a way that the material is elastic or extensible in this direction, but has inelastic reinforcing strips. In the applied state, the part A is intended to run substantially in the longitudinal direction of the arm, as will be shown later. The transverse direction is thus the effective direction of this part of the bandage.

The central part A has as a whole, or at least partially, a maximum elongation under tensile force of less than 30% in the transverse direction of the bandage.

The strips B, C, D and E may be arranged on the part A at an angle $\alpha$ of from 30 to 150°, with respect to the transverse direction of the bandage, all variations in the alignment of the respective strips being possible. They are, however, preferably perpendicularly disposed on the central part A, i.e. the angle $\alpha$ is 90° and the four long strips run parallel to one another.

The length of the strips is predetermined by their application technique, which is described more precisely further below. By way of example, the length of the bandage is altogether about 80 cm and it is about 12 cm wide. At the same time, the central part A is about 8 cm long and about 12 cm wide and the strips B, C, D and E are about 35 cm long and about 6 cm wide. Depending on the relative size of the arm to be bandaged, they may also be longer and wider or, if appropriate, be shortened. Furthermore, the strips (straps) may be differently designed, for example they may vary in thickness, width, length or the characteristic textile-related technical data.

The bandage is designed altogether in one piece, it either being cut out or punched out as a whole from a larger piece of bandage material or being joined together from individual parts.

It is particularly preferred for it to consist of a textile material which is extensible or elastic in one direction, i.e. the direction which is later the longitudinal direction of the bandage, preferably of a woven or nonwoven fabric which is extensible or elastic in this direction, in particular on a cotton base, having a maximum tensile strength of preferably at least 60 N/cm and an extensibility under loading of 10 N/cm of up to about 90%, preferably 10% to 80%, in the longitudinal direction. In the other direction, i.e. transversely thereto, the maximum elongation under tensile force should be at most 30%.

The material is at the same time aligned in the bandage such that the central part A is at least partially inelastic in the transverse direction and the strips B, C, D and E are extensible or elastic in the longitudinal direction. In the transverse direction, these strips are preferably inelastic. They may, however, also have elasticity or extensibility in this direction.

It has proven very favourable if a clearance in the form of a triangle is located at the inner end of the incision between the strips D and E, i.e. at the point of intersection of A, D and E. In this way, the fit of the bandage is improved and application made easier. The triangle is applied in such a way that its base runs along A transversely with respect to the longitudinal direction of the bandage and its vertex, pointing downwards, represents the end of the incision between D and E. It is preferably isosceles and also approximately equilateral. Its surface area is about 12 cm$^2$ and its corners may be rounded off. Other forms of clearance are also possible however. It is also possible to dispense entirely with the clearance or to provide only a small clearance.

There is advantageously likewise a small clearance at the inner end of the incision between the strips B and C, in order to prevent tearing.

On its side facing the skin, the bandage is coated with one of the known readily adhering self-adhesive compositions based on rubber or synthetic polymers. These should preferably be air-permeable and water-vapour-permeable and should have good skin compatibility.

Until the bandage is used, the adhesive layer may be covered with a sheet material treated so as to be adhesive-repellent, for example siliconized paper or plastic film.

It has proven favourable in this case to design this covering in several parts, preferably in 5 parts, by means of, for example, perforated separating lines. In this case, one part coverings the central part A and 4 further strip-shaped parts covering the narrower strips B, C, D and E. As an aid to application, the covering parts may be colour-marked or numbered.

When applying the bandage to the angled arm, the central part A is firstly fixed on the lateral side of the joint. This takes place in such a way that the central part A bisects widthwise—that is to say in the transverse direction—the limbs formed by the lower arm and upper arm and extends over the entire elbow joint. The triangular clearance is in this case to be aligned such that the epicondylus remains free. This makes it easier to adapt the bandage when applying it. Then, the strip B is led in a circular motion from medial to lateral around the upper arm and adhesively fixed, so that it encloses at least part of, preferably the entire upper arm at least once. The strips B, C, D, E are referred to as straps. As the next strap, the strip C is applied. This runs from medial to lateral on the lower arm, so that it encloses at least part of, preferably the entire lower arm and, if appropriate, also the back of the hand at least once. In the case of both straps B and C, it must be ensured that the inner bending region of the elbow is not adhesively coveringed.

Then the strap D is applied. It runs underneath the elbow distally to the lower arm and is led from there in a circular motion from medial to lateral. It is to enclose at least part of, preferably the entire lower arm at least once.

Finally the strap E is applied by being led proximally from the lower arm to the upper arm and there in a circular motion coming from medial to lateral.

The adhesive-repellent covering materials on the strips are successively removed in a way corresponding to the procedure when they are adhesively fixed. The bandage may additionally be strengthened by anchoring strips of customary tape material.

Once applied, the bandage supports, fixes and relieves the elbow joint, the restriction of the joint function being ensured by the strip A, which is at least partially inelastic in the transverse direction, while the strips B and C act in a fixing and supporting way, the strip D restricts the stretching of the lower arm and the strip E relieves the epicondylus. In addition, the bandage has a proprioceptive action and consequently supports the mechanical restriction of the joint function.

Simplified application of the ready-to-use bandage is also possible, however. In this case, the straps D and E are applied only in a circular motion around the lower or upper arm. By overlapping the straps B/D and C/E, fixing of the central part A is ensured even under severe loading. This overlapping can be achieved in a particularly simple way by a triangular shape of the covering on the self-adhesive side of the central part A. In this case, the straps B and C can additionally be led under the central part A. This strengthens the fixing.

The bandage according to the invention is represented by way of example in FIG. 1, the elongate strips (straps) B, C, D and E being arranged perpendicularly with respect to the central part A, i.e. the angle α is 90°. S denotes the point of intersection of A, D and E. The dashed lines indicate the perforation in the covering on the adhesive side of the bandage.

Figure 2:
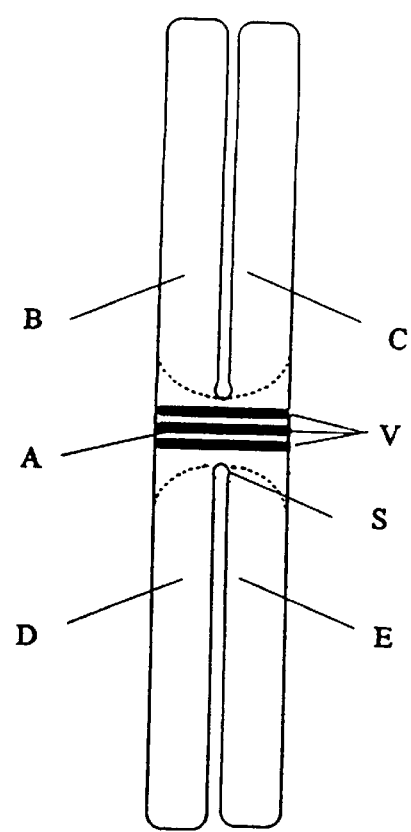

FIG. 2 shows by way of example a longitudinally and transversely elastic bandage having three inelastic reinforcing strips (V), which are joined to the bandage in the transverse direction in the central part A. As a result, the central part A is partially inelastic in the transverse direction and consequently effective in the way according to the invention.

Figure 3:
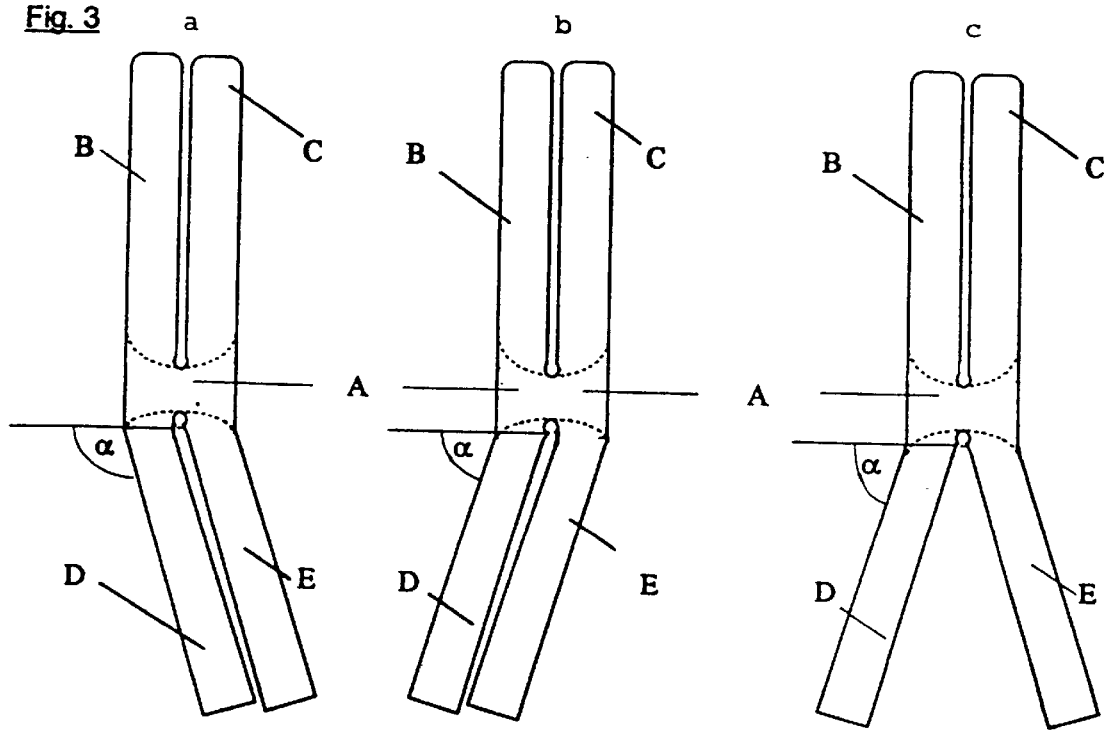

FIG. 3 shows under a, b and c three variations of the arrangement of the straps B, C, D and E with an angle α of the straps D and E with respect to the transverse direction of the bandage of in each case about 115° at a and in each case about 65° at b as well as about 65° for D and about 115° for E at c.

Figure 4:
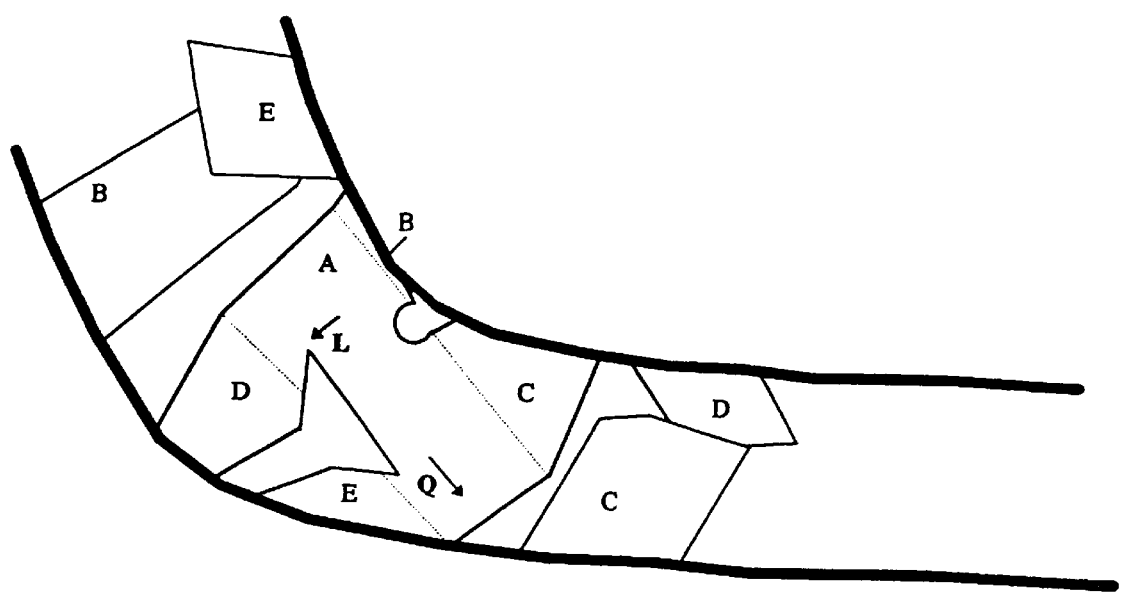

FIG. 4 shows the bandage in the applied state, wrapped around in the way described further above.

What is claimed is:

1. A method of relieving and functionally restricting the elbow joint of a patient in need thereof comprising the steps of:

providing a self-adhesive ready-to-use bandage comprising a substantially rectangular inelastic central part (A) having two opposite transverse sides and two opposite longitudinal sides, and having arranged on each of said two transverse sides two elongated strips, each of which is elastic in the longitudinal direction, at least one pair of the elongated strips having a clearance therebetween located in an inner end at the point of intersection with the inelastic central part (A);

attaching to the elbow joint when the elbow is held in an angled position, the self-adhesive bandage wherein the central part of the bandage is attached to the lateral side of the angled elbow joint and traverse to the direction of the upper and lower arms;

aligning the clearance such that the epicondylus remains free; and adhesively affixing said elongated strips to the upper and lower arms to thereby support, relieve and functionally fix the elbow joint.

2. The method of claim 1, wherein a first of said elongate strips on one transverse side of said part (A) is wrapped in a circular configuration from medial to lateral portions around the upper arm, a second of said elongate strips, adjacent to said first strip on said transverse side of said part (A), is wrapped in a circular configuration from medial to lateral portions around the lower arm, a third of said elongate strips, on the second transverse side of said part (A), is wrapped underneath said elbow distally to the lower arm and from there in a circular configuration from medial to lateral portions and a fourth of said elongate strips, adjacent to said third strip on said second transverse side of said part (A), is wrapped proximally from the lower arm to the upper arm and thence in a circular configuration from medial to lateral portions.

3. The method of claim 1, wherein a first of said elongate strips (B) on the first of the two transverse sides of central part (A) and a second elongate strip (D) on the second of the two transverse side of central part (A) and which is opposite said first elongate strip (B) are wrapped in a circular configuration around the upper arm, and the strips adjacent to each of said strips (C and E) are wrapped in a circular configuration around the lower arm.

* * * * *